US010546372B2

(12) United States Patent
Duckworth et al.

(10) Patent No.: US 10,546,372 B2
(45) Date of Patent: *Jan. 28, 2020

(54) METHOD, MACHINE, AND COMPUTER MEDIUM HAVING COMPUTER PROGRAM TO DETECT AND EVALUATE STRUCTURAL ANOMALIES IN CIRCUMFERENTIALLY WELDED PIPELINES

(71) Applicant: Kinder Morgan, Inc., Houston, TX (US)

(72) Inventors: Noel Duckworth, Richmond, TX (US); Tony Wright, Cypress, TX (US)

(73) Assignee: Kinder Morgan, Inc., Houston, TX (US)

( * ) Notice: Subject to any disclaimer, the term of this patent is extended or adjusted under 35 U.S.C. 154(b) by 1591 days.

This patent is subject to a terminal disclaimer.

(21) Appl. No.: 14/299,650

(22) Filed: Jun. 9, 2014

(65) Prior Publication Data

US 2014/0294285 A1 Oct. 2, 2014

Related U.S. Application Data

(60) Continuation-in-part of application No. 14/039,360, filed on Sep. 27, 2013, now Pat. No. 10,352,902, and
(Continued)

(51) Int. Cl.
*G01N 27/82* (2006.01)
*G06T 7/00* (2017.01)

(52) U.S. Cl.
CPC .................. *G06T 7/0004* (2013.01)

(58) Field of Classification Search
CPC ............ G01M 5/0025; G01M 5/0033; G01M 5/0091; G06T 7/0004; G01N 27/9046; G01N 27/83
(Continued)

(56) References Cited

U.S. PATENT DOCUMENTS 3,483,466 A   12/1969   Crouch et al.
3,539,915 A   11/1970   Walters et al.
(Continued)

OTHER PUBLICATIONS

Eiber, R., "Overview of Integrity Assessment Methods for Pipelines," Washington Cities and Counties Pipeline Safety Consortium, Nov. 2003, pp. 1-20). (Year: 2003).*
(Continued)

*Primary Examiner* — John E Breene
*Assistant Examiner* — Jeffrey P Aiello
(74) *Attorney, Agent, or Firm* — Bracewell LLP; Constance G. Rhegergen; Christopher L. Drymalla

(57) ABSTRACT

Embodiments of the present invention provide methods, machines, and a computer medium or media having computer programs to determine presence anomalies in circumferential welds of one or more pipelines transporting fluids associated with energy therethrough. Wave form analysis or pattern recognition in pipeline data such as magnetic flux leakage data is employed. A screening process, for example, does not affect or change how survey data is recorded such as in survey tools; only how it is analyzed after the survey data is completed. Embodiments of the machines, methods, and computer medium having computer programs can be used to screen for anomalies potentially threatening the structural integrity of the one or more pipelines so that site excavation can occur for confirmation and validation of the output results.

32 Claims, 8 Drawing Sheets
(5 of 8 Drawing Sheet(s) Filed in Color)

Related U.S. Application Data a continuation-in-part of application No. 12/953,720, filed on Nov. 24, 2010, now Pat. No. 9,243,972, and a continuation-in-part of application No. 12/949,896, filed on Nov. 19, 2010, now Pat. No. 8,140,273, said application No. 12/953,720 is a continuation of application No. 12/949,896, filed on Nov. 19, 2010, now Pat. No. 8,140,273, and a continuation of application No. 12/950,118, filed on Nov. 19, 2010, now Pat. No. 9,581,520, application No. 14/299,650, which is a continuation-in-part of application No. 12/950,118, filed on Nov. 19, 2010, now Pat. No. 9,581,520, and a continuation-in-part of application No. 12/270,432, filed on Nov. 13, 2008, now Pat. No. 7,899,628, said application No. 12/949,896 is a division of application No. 12/270,432, filed on Nov. 13, 2008, now Pat. No. 7,899,628, said application No. 12/950,118 is a continuation of application No. 12/270,432, filed on Nov. 13, 2008, now Pat. No. 7,899,628, said application No. 12/953,720 is a continuation of application No. 12/270,432, filed on Nov. 13, 2008, now Pat. No. 7,899,628.

(60) Provisional application No. 61/864,095, filed on Aug. 9, 2013, provisional application No. 61/706,575, filed on Sep. 27, 2012, provisional application No. 61/008,822, filed on Dec. 21, 2007.

(58) Field of Classification Search
USPC ............... 73/592, 622, 623; 324/238, 240; 382/152; 702/34, 35, 39
See application file for complete search history.

(56) References Cited

U.S. PATENT DOCUMENTS

| | | | |
|---|---|---|---|
| 3,753,085 A | 8/1973 | Morton et al. | |
| 3,762,446 A | 10/1973 | Tungseth et al. | |
| 4,241,430 A | 12/1980 | Kayem et al. | |
| 4,507,019 A | 3/1985 | Thompson | |
| 4,885,723 A | 12/1989 | Havira et al. | |
| 5,182,775 A | 1/1993 | Matsui et al. | |
| 5,323,429 A | 6/1994 | Roarty et al. | |
| 5,479,100 A | 12/1995 | Fowler et al. | |
| 5,526,689 A | 6/1996 | Coulter et al. | |
| 5,571,955 A | 11/1996 | Beavers et al. | |
| 5,587,534 A | 12/1996 | McColskey et al. | |
| 5,728,943 A | 3/1998 | Colter, Jr. et al. | |
| 5,751,144 A | 5/1998 | Weischedel | |
| 5,883,311 A | 3/1999 | Hettiarachchi et al. | |
| 5,883,815 A | 3/1999 | Drakulich et al. | |
| 5,943,632 A | 8/1999 | Edens et al. | |
| 6,021,093 A | 2/2000 | Birchak et al. | |
| 6,107,811 A | 8/2000 | Caudill et al. | |
| 6,155,292 A | 12/2000 | Kurata | |
| 6,205,859 B1* | 3/2001 | Kwun | G01N 29/2412 73/579 |
| 6,243,657 B1 | 6/2001 | Tuck et al. | |
| 6,373,245 B1 | 4/2002 | Kwun et al. | |
| 6,405,156 B1 | 6/2002 | Kern et al. | |
| 6,429,650 B1* | 8/2002 | Kwun | G01N 29/11 324/220 |
| 6,597,997 B2 | 7/2003 | Tingley | |
| 6,727,691 B2 | 4/2004 | Goldfine et al. | |
| 6,995,557 B2 | 2/2006 | Goldfine et al. | |
| 7,013,249 B1 | 3/2006 | Davis | |
| 7,231,331 B2 | 6/2007 | Davis | |
| 7,626,383 B1* | 12/2009 | Sun | G01N 27/82 324/232 |
| 7,899,628 B2 | 3/2011 | Duckworth et al. | |
| 8,140,273 B2 | 3/2012 | Duckworth et al. | |
| 9,243,972 B2 | 1/2016 | Duckworth et al. | |
| 2001/0022514 A1* | 9/2001 | Light | G01N 17/006 324/240 |
| 2003/0025913 A1* | 2/2003 | Izatt | A61B 5/0066 356/479 |
| 2003/0198374 A1* | 10/2003 | Hagene | G01N 21/954 382/141 |
| 2004/0076390 A1* | 4/2004 | Dong Yang | A61B 1/00096 385/116 |
| 2004/0095137 A1* | 5/2004 | Kwun | G01N 29/11 324/240 |
| 2006/0076951 A1 | 4/2006 | Nestleroth et al. | |
| 2007/0165234 A1* | 7/2007 | Podoleanu | A61B 3/102 356/451 |
| 2007/0222436 A1* | 9/2007 | Gao | G01N 27/82 324/220 |
| 2007/0223643 A1* | 9/2007 | Yamane | G01M 5/0025 376/249 |
| 2009/0234590 A1 | 9/2009 | McNealy et al. | |
| 2011/0062951 A1 | 3/2011 | Duckworth et al. | |
| 2011/0068782 A1 | 3/2011 | Duckworth et al. | |
| 2011/0098941 A1 | 4/2011 | Duckworth et al. | |
| 2014/0062792 A1* | 3/2014 | Schantz | G01S 5/0252 342/451 |
| 2014/0088889 A1 | 3/2014 | Duckworth | |
| 2014/0294285 A1 | 10/2014 | Duckworth et al. | |

OTHER PUBLICATIONS

Edwards, G., "Detection of corrosion in offshore risers using guided ultrasonic waves," International Conference on Offshore Mechanics and Arctic Engineering, OMAE 2007, San Diego, CA, Jun. 10-15, 2007, pp. 1-17). (Year: 2007).*

Final Office Action for co-pending U.S. Appl. No. 12/950,118 dated Jul. 9, 2014.

Office Action for co-pending U.S. Appl. No. 12/950,118 dated Mar. 23, 2015.

Office Action for co-pending U.S. Appl. No. 12/953,720 dated Feb. 27, 2015.

M. Beller, Tools, Vendors, Services—A Review of Current In-Line Inspection Technologies, Copyright 2002, Pigging Products and Services Association, 13 pages.

Specifications and requirements for intelligent pig inspection of pipelines, Version 3.2, Jan. 2005, 30 pages.

Amineh et al. "Characterization of Surface Breaking Cracks Using One Tangential Component of Magnetic Leakage Field" IEEE Trans. Magnetics, Oct. 15, 2007, pp. 1-9.

Budenkov et al. "Use of Rayleigh Waves in Testing Stress-Corrosion Breaks in Pipelines by the Acoustic Emission Method" Russian Journal of Nondestructive Testing, vol. 36, No. 10, Jan. 10, 2000, pp. 763-768.

Co-pending U.S. Appl. No. 12/953,720, filed Nov. 24, 2010.

Co-pending U.S. Appl. No. 14/039,360, filed Sep. 27, 2013.

Czyz et al. "Multi-Pipeline Geographical Information System Based on High Accuracy Inertial Surveys" Proceedings of IPC 2000, International Pipeline Conference, Calgary, Oct. 2000, ASME Paper No. IPC00-138, pp. 1-5.

Eiber, Bob "Overview of Integrity Assessment Methods for Pipelines" Washington Citites and Counties Pipeline Safety Consortium, Nov. 2003, 20 pages.

Evertz et al. "Test method for the investigation of the susceptibility to cracking in near neutral pH solution" Steel Research, vol. 70, No. 4+5, Apr./May 1999, pp. 183-187.

Leeds et al. "Modified analysis method helps coating fault, pipe assessment" Corrosion & Pipe Protection, vol. 83, No. 3, Mar. 2000, 11 pgs.

Leis et al. "Stress-Corrosion Cracking on Gas-Transmission Pipelines: History, Causes, and Mitigation" Proceedings, First International Business Conference on Onshore Pipelines, Berlin, Dec. 1997, 17 pgs.

Marr et al. "Procedures guide prediction, evaluation of stress corrosion" Corrosion & Pipe Protection, vol. 81, No. 3, Mar. 1998, 14 pgs.

(56) References Cited

OTHER PUBLICATIONS

Office Action for co-pending U.S. Appl. No. 12/950,118 dated Mar. 10, 2014.
Roberts, Brian "Monitoring the quality of welded tube and pipe" TheFabricator.com, Sep. 17, 2001, 8 pages.
Shi et al., "Theory and Application of Magnetic Flux Leakage Pipeline Detection", Sensors, 2015, pp. 31036-31055, vol. 15.

* cited by examiner

METHOD, MACHINE, AND COMPUTER MEDIUM HAVING COMPUTER PROGRAM TO DETECT AND EVALUATE STRUCTURAL ANOMALIES IN CIRCUMFERENTIALLY WELDED PIPELINES

CROSS-REFERENCE TO RELATED APPLICATIONS

This application claims priority to and the benefit of U.S. Provisional Patent Application Ser. No. 61/864,095, titled "System, Method and Computer Medium Having Computer Program to Detect and Evaluate Structural Anomalies in Circumferentially Welded Pipelines" filed on Aug. 9, 2013, which hereby is incorporated herein by reference in its entirety. This application also is a continuation-in-part of U.S. patent application Ser. No. 14/039,360 titled "System, Method and Computer Medium Having Computer Program to Determine Presence of Stress Corrosion Cracking in Pipelines With Pattern Recognition" filed on Sep. 27, 2013, which claims priority to and the benefit of U.S. Provisional Patent Application Ser. No. 61/706,575 filed on Sep. 27, 2012. This application also is a continuation-in-part of U.S. patent application Ser. No. 12/953,720 titled "Computer-Implemented Method to Screen for Longitudinal-Seam Anomalies" filed on Nov. 24, 2010, which is a continuation of then U.S. patent application Ser. No. 12/270,432, a continuation of then U.S. patent application Ser. No. 12/949,896, and a continuation of U.S. patent application Ser. No. 12/950,118. This application also is a continuation-in-part of U.S. patent application Ser. No. 12/950,118 titled "System to Screen for Longitudinal-Seam Anomalies" filed on Nov. 19, 2010, which is a continuation of then U.S. patent application Ser. No. 12/270,432. This application also is a continuation-in-part of U.S. patent application Ser. No. 12/949,896 (now U.S. Pat. No. 8,140,273) titled "Program Product to Screen for Longitudinal-Seam Anomalies" filed on Nov. 19, 2010, which is a divisional of then U.S. patent application Ser. No. 12/270,432. This application also is a continuation-in-part of U.S. patent application Ser. No. 12/270,432 (now U.S. Pat. No. 7,899,628) titled "System, Method and Program Product to Screen for Longitudinal-Seam Anomalies" filed on Nov. 13, 2008, which claims priority to and the benefit of U.S. Provisional Patent Application Ser. No. 61/008,822 filed on Dec. 21, 2007. The contents of the above-identified applications hereby are incorporated herein by reference in their entireties.

BACKGROUND

1. Field of Invention

The present invention relates to the detection and evaluation of anomalies such as cracks and incomplete fusions in welds of pipelines, e.g., pipelines for the transport of fluids associated with energy or other resources. In particular, the invention relates to methods, machines, and computer media having computer programs which utilize signal wave form and pattern recognition to detect and locate anomalies such as with axial magnetic flux leakage technology.

2. Description of Related Art

Some pipelines with segments that have been joined by welding have experienced in-service failures due to anomalies such as incomplete fusion and cracks. Some of the anomalies that potentially pose threats to the integrity of a pipeline have been difficult to detect and distinguish from other anomalies with some current pipeline inspection tools and methods.

Magnetic Flux Leakage (MFL) inspection is often a robust and reliable inspection technology, which can be used effectively to detect 'crack-like' defects in the welds and other locations within a pipeline wall.

Generally, MFL technology operates on the principle that where there is metal loss in the pipeline, a magnetic field leaks from the metal. To implement MFL inspection technology in a pipeline, an MFL tool such as an In-Line Inspection (ILI) tool is often deployed into an interior of the pipeline and induced to travel therethrough to evaluate the pipeline wall. In some instances, the MFL tool includes magnets and brushes arranged to create a magnetic circuit with the pipeline wall and to saturate the pipeline wall with magnetic flux. Longitudinal or circumferential field paths are induced depending on the needs of a particular pipeline survey. For example, strategically placed sensors on the MFL tool can detect signals representative of the leakage of the magnetic flux from the pipeline wall at locations around a circumference of the pipeline wall over a length of the pipeline. Because anomalies, such as metal loss within the pipeline wall, tend to change the MFL signals detected in proportion to the size of the anomaly, the MFL signals detected from the pipeline wall can be analyzed to determine the size and location of anomalies within the pipeline wall. An example of an advanced data analysis technique associated with MFL technology, and developed by Applicant, can be seen in U.S. Pat. No. 7,899,628 titled "System, Method and Program Product to Screen for Longitudinal-Seam Anomalies" and U.S. Pat. No. 8,140,273 titled "Program Product to Screen for Longitudinal-Seam Anomalies," which hereby are incorporated herein by reference in their entireties.

In normal analysis processes utilizing Axial Flux MFL (A-MFL) technology, on the other hand detection processes have been primarily focused on the identification and quantification of volumetric metal loss anomalies along a pipeline. This technology utilizes the amount of flux leakage detected, the length of anomaly, and the width of anomaly (number of channels) to determine depth.

SUMMARY OF INVENTION

In view of the foregoing, Applicant recognized that when a "metal-loss" sizing algorithm is applied to narrow axial anomalies such as cracks in a circumferential weld (girth weld), for example, the resulting calculated depth can be considerably shallower than the actual depth. Because there are a limited number of channels affected by these anomalies, the calculated depth is low and most often below a minimum reporting threshold. Additionally, when the data indicative of these anomalies that are potentially threatening to the structural integrity of the pipeline is displayed, the data is often obscured by data from adjacent portions of the pipeline. These factors contribute to non-reported anomalies, which may lead to pipeline failures. Accordingly, Applicant also recognized a need for a new identification machine, process, and technology that overcomes the above-identified limitations, among others. Accordingly, embodiments of the present invention provide methods, machines, and computer media having computer programs to detect anomalies that are potentially threatening to the structural integrity of one or more pipelines or portions thereof such as circumferential welds by utilizing pattern recognition in pipeline data such as A-MFL data. A screening process, for example, does not affect or change how survey data is recorded such as in survey tools; only how it is analyzed after the collection of the survey data is completed. Embodiments of the methods, machines, and computer media having computer programs can be used to screen for circumferential welds that are candidates for site excavation to confirm and validate the analysis of those welds.

Embodiments of the present invention also provide methods, machines and computer media having computer programs which utilize wave form analysis or pattern recognition to detect potentially threatening anomalies in circumferential welds. For example, according to an embodiment of the present invention, a pattern recognition protocol can use axially scanned images generated from A-MFL data to locate circumferential welds with an elevated potential of containing cracks or other potentially threatening anomalies.

An embodiment of a method of detecting and evaluating anomalies in circumferential welds of a longitudinally extending pipeline for the transport of fluids associated with energy therethrough includes (i) receiving, in a first process, magnetic flux leakage data from one or more pipeline inspection survey tools, the magnetic flux leakage data including data being associated with one or more circumferential welds of one or more longitudinal pipelines, (ii) displaying, in a second process, the magnetic flux leakage data on the one or more displays as one or more A-Scan images whereby each of a plurality of channels is being represented by a respective one of a plurality of individual lines and whereby deviations in paths of the individual lines represent an excess or absence of metal in the structure of the one or more longitudinal pipelines, (iii) identifying, in a third process, one or more weld regions in the one or more A-Scan images including the magnetic flux leakage data representing the one or more circumferential welds, (iv) analyzing, in a fourth process, the magnetic flux leakage data within the one or more weld regions of the one or more A-Scan images being displayed on the one or more displays by making a determination whether anomalous regions can be detected within the one or more weld regions that include one or more individual lines that deviate from respective paths in a manner dissimilar to a background array of lines, and (v) generating, in a fifth process, an output on a display to identify a location of any of the one or more circumferential welds corresponding to any of the one or more weld regions in which an anomalous region was detected in the fourth process.

An embodiment of a machine to detect anomalies in circumferential welds in a longitudinally extending pipeline associated with the transport of fluids associated with energy or other resources therethrough, for example, can include one or more displays, one or more processors in communication with the one or more displays and being adapted to process data received from one or more pipeline inspection survey tools, and non-transitory storage medium or media having one or more computer programs stored thereon and readable by the one or more processors. The one or more computer programs can include a set of instructions that, when executed by the one or more processors, causes the one or more processors to perform the operations of: (i) receiving, in a first process, magnetic flux leakage data from the one or more pipeline inspection survey tools related to one or more circumferential welds in one or more longitudinal pipelines, (ii) displaying, in a second process, the magnetic flux leakage data on the one or more displays as one or more selected patterns of data representing selected signal characteristics of the one or more circumferential welds, (iii) analyzing, in a third process, the magnetic flux leakage data responsive to the selected signal characteristic and one or more predetermined patterns of the magnetic flux leakage data of the pipeline joint being displayed on the one or more displays, the one or more predetermined patterns of the magnetic flux leakage data being indicators of one or more anomalies potentially threatening the structural integrity of the pipeline, and (iv) generating, in a fourth process, an output identifying a location and characterization of the one or more anomalies identified.

An embodiment of a method of detecting and evaluating anomalies in circumferential welds of a longitudinally extending pipeline for the transport of fluids associated with energy therethrough, for example, can include (i) receiving, in a first process, magnetic flux leakage data from the one or more pipeline inspection survey tools, the magnetic flux leakage data being associated with one or more circumferential welds of one or more longitudinal pipelines, (ii) displaying, in a second process, the magnetic flux leakage data on the one or more displays as one or more selected patterns of data representing selected signal characteristics of the one or more circumferential welds, (iii) analyzing, in a third process, the magnetic flux leakage data of the one or more circumferential welds being displayed on the one or more displays by making a determination whether the displayed patterns of data are consistent with one or more predetermined patterns of magnetic flux leakage data, the one or more predetermined patterns of the magnetic flux leakage data being indicators of one or more anomalies within the one or more circumferential welds that are potentially threatening the structural integrity of the pipeline, (iv) generating, in a fourth process, an output identifying a location and characterization of any of the one or of more circumferential welds for which the displayed patterns of data was determined to be consistent with the one or more predetermined patterns in the third process, and (v) validating, in a fifth process, the output by excavating one or more of the circumferential welds identified in the output and inspecting the one or more of the circumferential welds excavated to confirm the presence of one or more anomalies within the one or more or the circumferential welds excavated that are potentially threatening the structural integrity of the pipeline.

An embodiment of a non-transitory storage medium or media having one or more computer programs stored thereon and readable by one or more processors, may include, for example, one or more computer programs including a set of instructions that, when executed by the one or more processors, causes the one or more processors to perform the operations of (i) receiving, in a first process, magnetic flux leakage data from the one or more pipeline inspection survey tools, the magnetic flux leakage data being associated with one or more circumferential welds of one or more longitudinal pipelines, (ii) displaying, in a second process, the magnetic flux leakage data on the one or more displays as one or more selected patterns of data representing selected signal characteristics of the one or more circumferential welds, (iii) analyzing, in a third process, the magnetic flux leakage data of the one or more circumferential welds being displayed on the one or more displays by making a determination whether or not the displayed patterns of data are consistent with one or more predetermined patterns of magnetic flux leakage data, the one or more predetermined patterns of the magnetic flux leakage data being indicators of anomalies within the one or more circumferential welds that are potentially threatening the structural integrity of the pipeline, and (iv) generating, in a fourth process, an output identifying a location and characterization of any of the one or of more circumferential welds for which the displayed patterns of data was determined to be consistent with the one or more predetermined patterns of in the third process.

Embodiments of methods, machines, and computer media having computer programs, for example, can include an identification process developed through utilization of A-MFL inspection technology taken to a new level of sophistication with a disciplined methodical evaluation of data and data signals. Particularly, for example, embodiments of the present invention can include supplemental screening processes applied to pipeline survey data, which utilize an A-MFL method and wave form analysis or pattern recognition to identify anomalies in circumferential welds potentially threatening the structural integrity of the pipeline. The screening process of embodiments of the present invention does not need to affect or change how the survey data is recorded in the ILI survey tools or other pipeline inspection tools if that is not desired; only how it is analyzed after the collection of survey data is completed.

Embodiments of methods, machines, and computer media having computer programs of the present invention, can include confirmation and validation of the process applicability in each case. The confirmation, for example, minimally can include several validation excavations utilizing "highest level" Non-Destructive Evaluation ("NDE") methods and, in some cases, can require removal of appropriate samples for destructive metallurgical evaluation in a laboratory.

BRIEF DESCRIPTION OF DRAWINGS

The patent or application file contains at least one drawing executed in color. Copies of this patent or patent application publication with color drawing(s) will be provided by the Patent and Trademark Office upon request and payment of the necessary fee. Some of the features and benefits of the present invention having been stated, others will become apparent as the description proceeds when taken in conjunction with the accompanying drawings, in which.

DETAILED DESCRIPTION OF INVENTION

The present invention will now be described more fully hereinafter with reference to the accompanying drawings in which embodiments of the invention are shown. This invention may, however, be embodied in many different forms and should not be construed as limited to the illustrated embodiments set forth herein; rather, these embodiments are provided so that this disclosure will be thorough and complete, and will fully convey the scope of the invention to those skilled in the art. Like numbers refer to like elements throughout.

An embodiment of the present invention, for example, can include a supplemental screening process applied to survey data utilizing display software, such as, for example, the ROSEN ROSOFT for Pipelines display software manufactured by ROSEN Swiss AG of Stans, Switzerland (such as, for example, version 6.60), as understood by those skilled in the art, to detect and locate anomalies in circumferential pipeline welds having an elevated potential of threatening the structural integrity of the pipeline. The ROSEN ROSOFT display software may be employed to display data collected by ROSEN USA, a pipeline inspection service provider that identifies one of their circumferential field tools as "Corrosion Detection Pig" (CDP). Although embodiments of the present invention are described in conjunction a single software provider package, other forms of display software can be utilized as well as will be understood by those skilled in the art.

Figure 1:
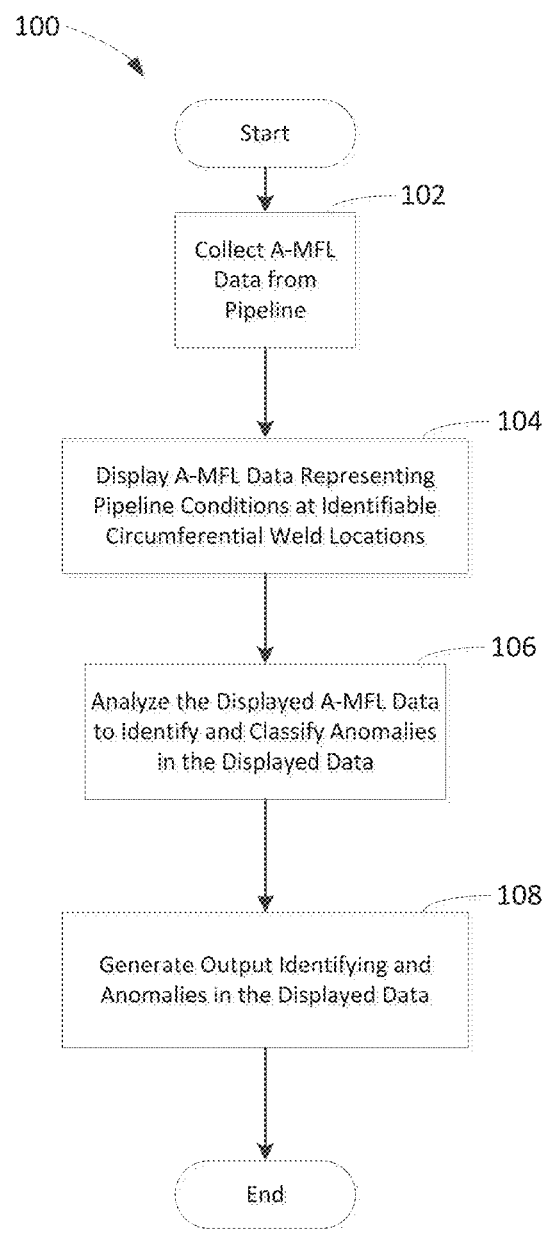
FIG. 1 is a flow chart illustrating one exemplary method to determine locations having an elevated potential of containing threatening anomalies in one or more circumferential pipeline welds according to an embodiment of the present invention.

An embodiment of a method 100 of the present invention, for example, such as shown in FIG. 1, can begin by collecting A-MFL data from a pipeline (step 102) using a survey tool, such as, for example, an inline inspection ("ILI") tool as understood by those skilled in the art. The A-MFL data, for example, can be primarily influenced by anomaly air gaps, which are a function of anomaly length and depth, steel properties, and hoop stress. Once the A-MFL data has been collected using the survey tool at step 102, as understood by those skilled in the art, it can be transmitted to one or more computers having one or more processors (see, for example, processor 306 depicted in FIG. 8), as understood by those skilled in the art, for analysis. Such a transmission can be achieved via any number of wired or wireless communications techniques. At step 104, the processor then causes the A-MFL data to be displayed on a display, such as one or more electronic displays, display region, or the like, as understood by those skilled in the art, as one or more patterns of data representing pipeline conditions at identifiable circumferential weld locations. The pipeline conditions displayed are based on -MFL signal characteristics detected by the survey tool. As indicated in greater detail below, these signal characteristics can be displayed as, in some embodiments, line traces on an A-Scan image so that each channel is being represented by one or more individual lines.

At step 106, the A-MFL data is analyzed based upon its respective signal characteristics. In embodiments, an advanced data analysis technique known as Kinder Morgan's KMAP process is performed by the processor. Portions of the KMAP process are defined in Protocol PI 3, "KMAP Screening for Long Seam Anomaly Evaluation, ROSEN Software Package," (and incorporated herein by reference) and generally is employed in conjunction with a body scan and a longitudinal weld scan for evaluating the integrity of longitudinal welds in the pipeline. Based on the results of the KMAP Protocol, as understood by those skilled in the art, embodiments of machines, methods, and computer media having computer programs can additionally analyze the A-MFL data associated with one or more circumferential welds in the pipeline to determine if patterns indicative of potentially elevated risks of threatening anomalies are found to be contained in the data. One or more exemplary embodiments of these patterns are illustrated in FIGS. 2-6. At step 108, for example, an output is generated including a list of potentially threatening anomalies in the pipeline. Such an output can typically be a summary display or spreadsheet, associated screen captures and suggested excavation locations. The process 100 ends after step 108, although in other embodiments, such as in the method 200 described below with reference to FIG. 7, the method can be iteratively refined after excavating and evaluating one or more pipeline joints as recommended in the output generated in step 108.

Figure 2:
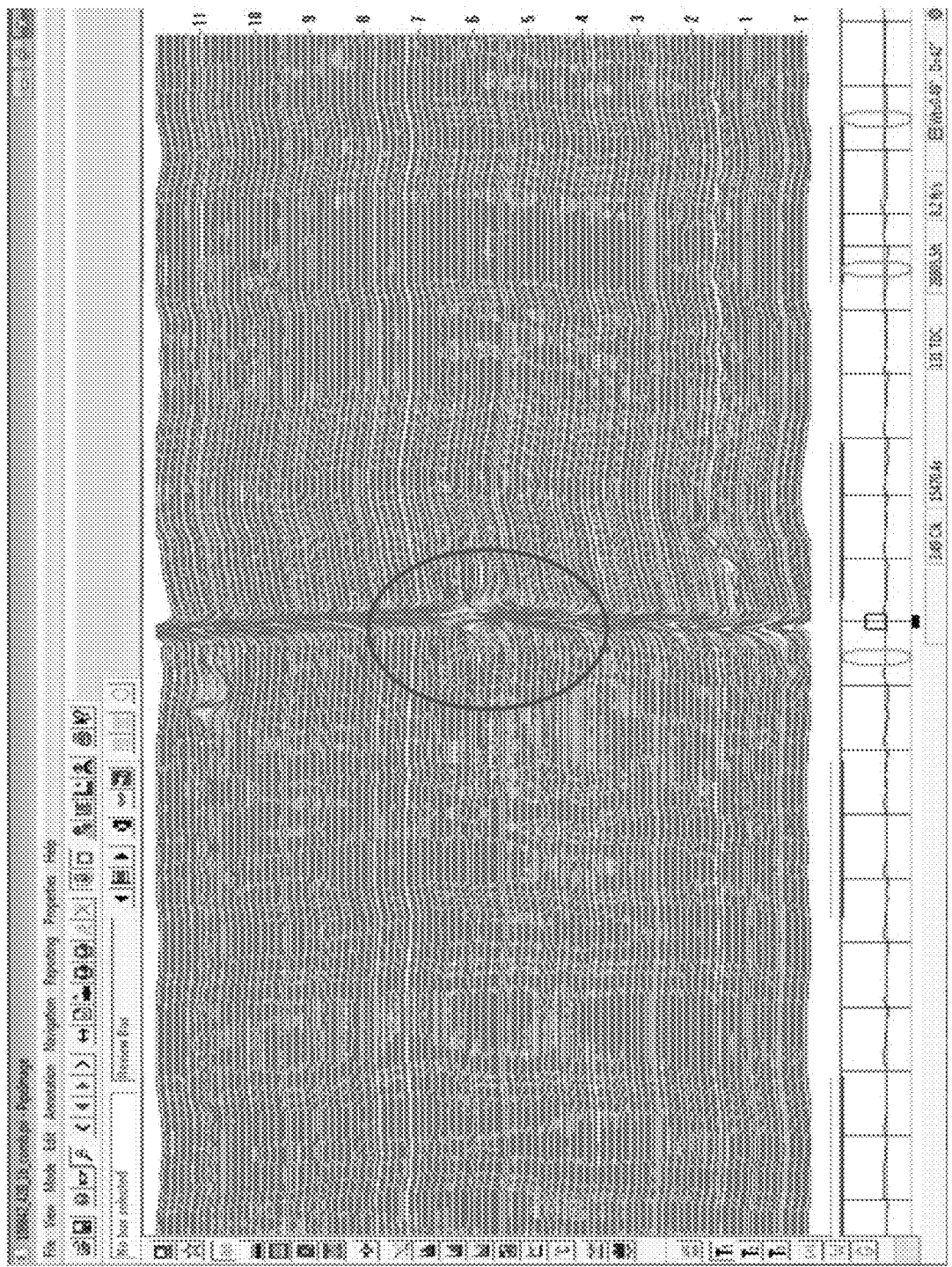
FIG. 2 is a graphical view of an Axial-Scan (A-Scan) computer display showing magnetic flux leakage data indicative of a level-one pipeline anomaly in a circumferentially welded seam whereby the x-axis corresponds to a longitudinal position along the pipeline and the y-axis corresponds to both a circumferential or radial position about the pipeline and to an amplitude of a magnetic flux leakage signals according an embodiment of the invention.

FIG. 2 illustrates an example of an A-Scan computer display showing the A-MFL data from one pipeline location having a circumferential weld known to contain a crack-like anomaly that is potentially threatening to the pipeline being depicted. The x-axis in FIG. 2 represents a longitudinal location along the pipeline, and the y-axis represents a circumferential location about a full 360 degree circumference of the pipeline wall. Each channel of the A-MFL data collected is represented as an individual line extending in a generally horizontal direction from an upstream location (generally to the left in FIG. 2) to a downstream location (generally to the right in FIG. 2), for example.

A weld region can be identified in FIG. 2 in locations where data representative of a circumferential weld is being displayed. The weld region in FIG. 2 includes the centrally located, generally vertical feature formed from fluctuations in each of the lines representing the individual channels. At the longitudinal location of the circumferential weld, the lines generally deviate upwardly from the general horizontal direction. The upward deviation is an indication of the excess metal that would be expected at a weld location as compared to the metal content of the surrounding upstream and downstream locations in the pipeline structure. The upward deviation of most of the lines for example, can be indicative of signals that may be characterized as "low frequency" as the upward deviation is gradual at the central weld location.

A suspected anomalous region in the weld region of FIG. 2 can be identified as indicated by an oval circumscribing the anomaly in FIG. 2. In some of the channels representing the anomaly, the upward deviation appears slightly to the right, or on an upstream side of the circumferential weld. These channels or individual lines deviate from respective paths in a manner dissimilar to a background array of lines. From the view depicted in FIG. 2, no meaningful assessment can be made for the potential anomaly that would indicate whether the anomaly represents a defect in the weld that could threaten the structural integrity of the pipeline. Thus, the view in FIG. 2 can be used in some embodiments of a method to characterize the anomaly as a level-one anomaly, which merits further analysis by clarification of the image and further analysis of the data.

Figure 3:
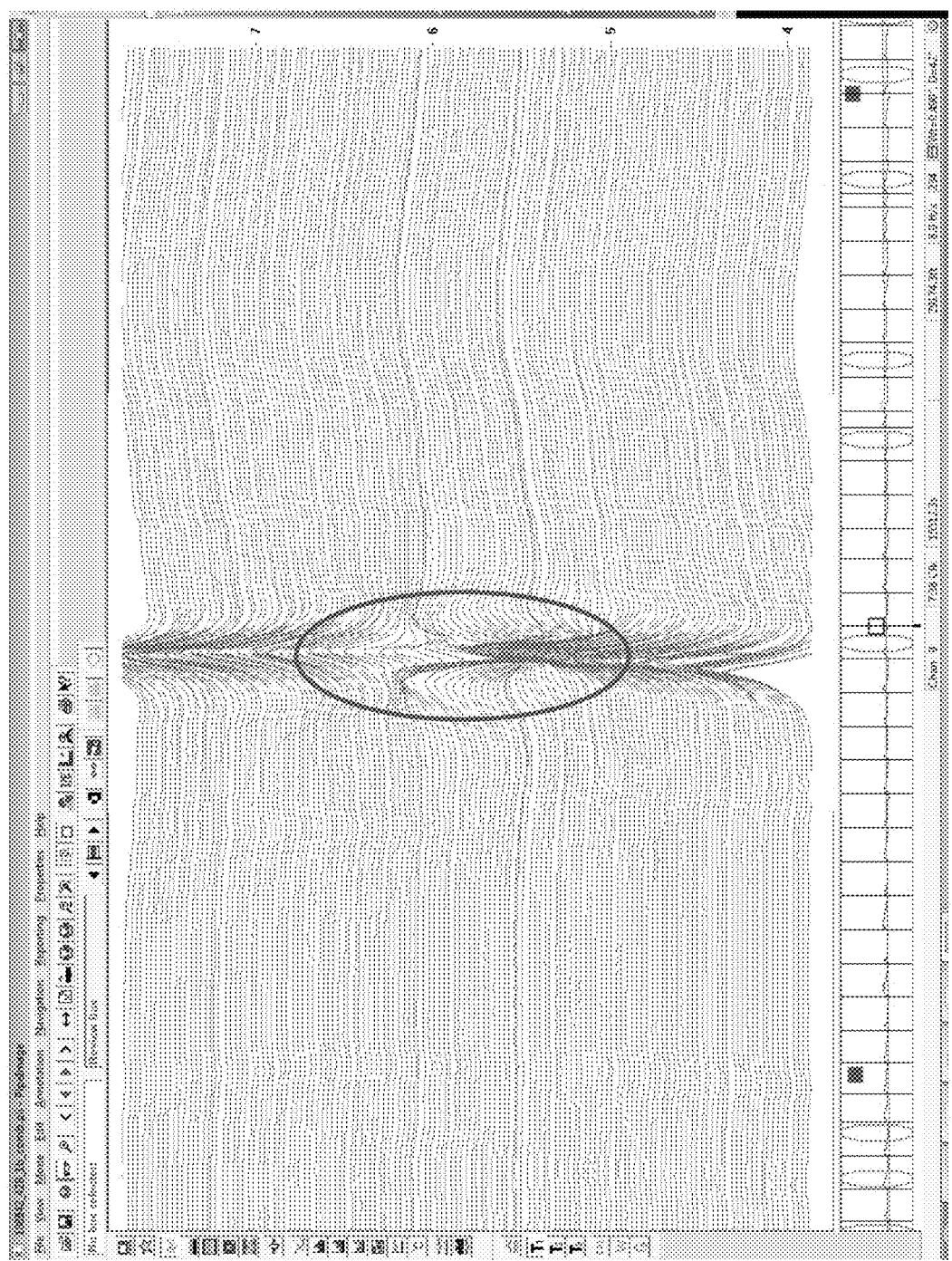
FIG. 3 is a graphical view of an A-Scan computer display showing the magnetic flux leakage data depicted in FIG. 2 displayed in a manner indicative of a level-two pipeline anomaly according to an embodiment of the present invention.

FIG. 3 illustrates the suspected anomalous area being identified in the circumferential weld and being enlarged in comparison to the view depicted in FIG. 2 such that only approximately one third of the circumference (120 degrees) of the pipeline wall is depicted. This view is sufficient to encompass the data representing the anomaly and indicates that some of the lines deviate downwardly within the region. This downward deviation is an indication of an anomalous gap in the metallic structure of the pipeline. The lines appear to slope gradually downwardly in a manner consistent with the lines representing the low frequency A-MFL signals of the upwardly sloping lines indicating excess metal in the circumferential weld. This view is also adequate for an analyst to determine that the location represented is worthy of further investigation by excavating the pipeline and visually inspecting the pipeline, or otherwise evaluating the structural integrity of the pipeline by NDE methods and, in some cases, may require removal of appropriate samples for destructive metallurgical evaluation in a laboratory. Thus, the view in FIG. 3 can be used in some embodiments of a method to characterize the anomaly as a level-two anomaly, which merits further analysis by excavation and inspection.

Figure 4:
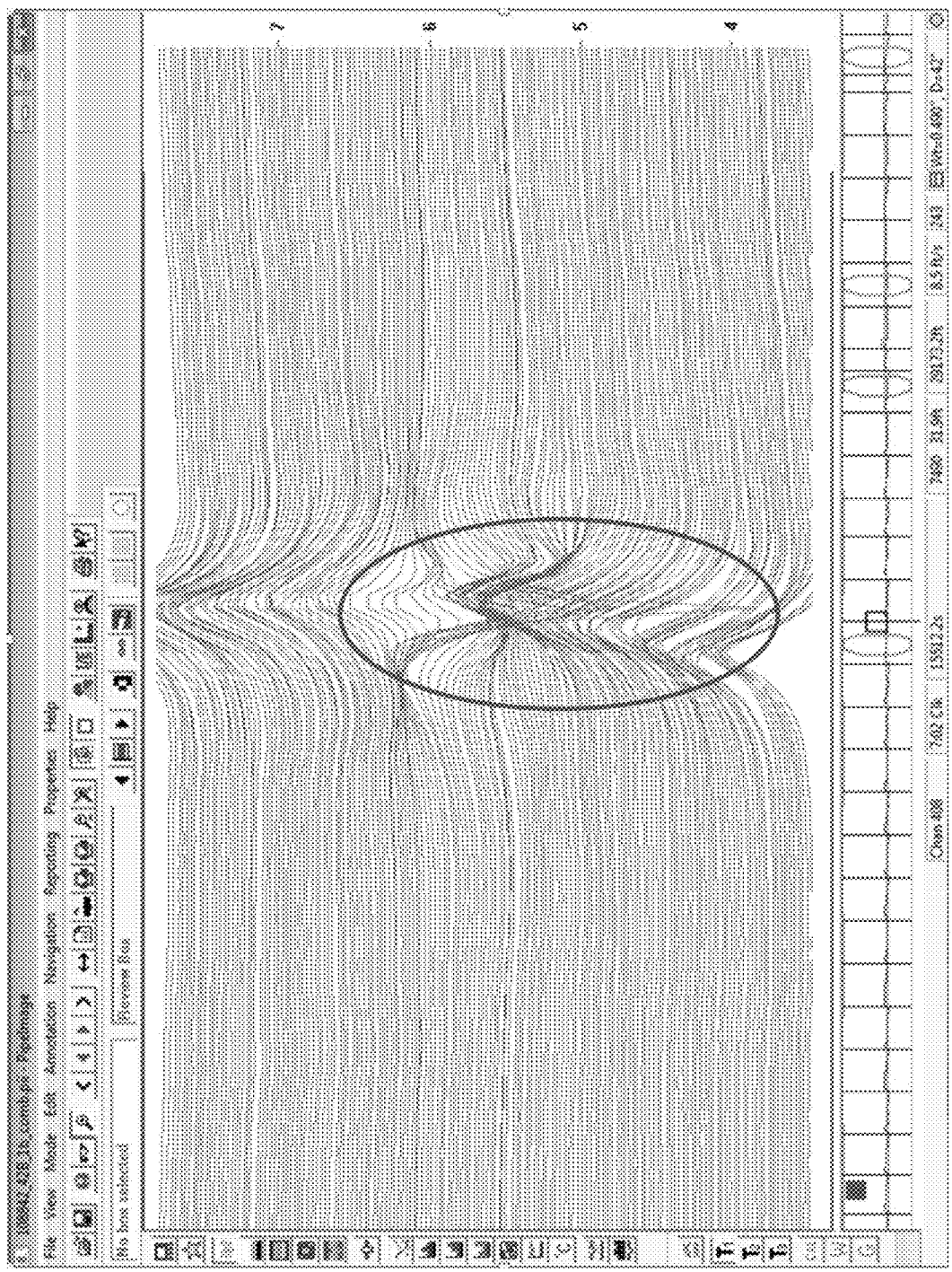
FIG. 4 is a colored graphical view of an A-Scan computer display showing the magnetic flux leakage data depicted in FIGS. 2 and 3 displayed in a manner indicative of a level-three pipeline anomaly, whereby each channel within the anomalous area is isolated and colored for greater visibility according to an embodiment of the present invention.

FIG. 4 illustrates one or more suspected anomalous areas identified in the circumferential weld being enlarged in comparison to the view depicted in FIG. 3 such that a lesser extent of the longitudinal length of the pipeline is represented in the display. Each channel within the magnetic anomalous area is isolated and displayed in a distinguishing color with respect to the surrounding channels. In this view of FIG. 4, it is apparent to those skilled in the art that high frequency signals are present within the larger, low frequency array of signals represented. These relatively high-frequency signals can be indicators of crack-like defects in the circumferential weld that potentially threaten the structural integrity of the pipeline. The exact range of frequencies that indicate crack-like defects can depend on many variables including variables associated with the construction of the pipeline, the type of inspection performed, and other factors as will be understood by those skilled in the art. A relative analysis of the high-frequency signals with respect to surrounding low-frequency signals accounts for variations in many of these variables. The views depicted in FIGS. 2 and 3 obscure the presence of these high-frequency signals, which are prominently displayed in FIG. 4. Thus, the view in FIG. 4 can be used in some embodiments of a method to characterize the anomaly as a level-three anomaly. Level-three anomalies can be defined to include those anomalies consistent with crack like defects that potentially threaten the structural integrity of a longitudinal pipeline. In-line-inspection vendors do not generally identify these potentially threatening defects in pipeline welds, but the discipline of the KMAP process has been further developed to include processes to identify, display and clarify these indicators as noted and described herein.

Figure 5:
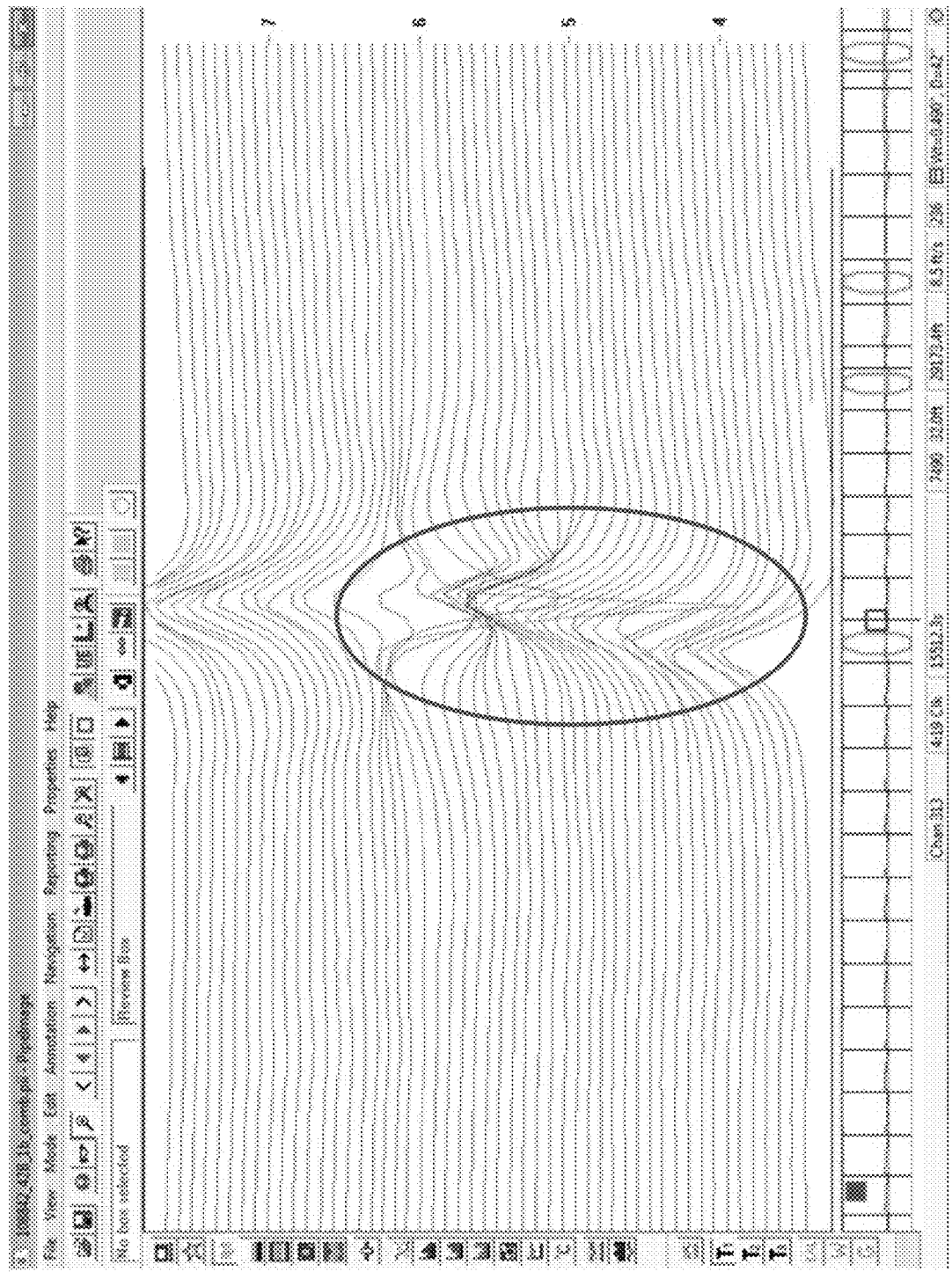
FIG. 5 is a colored graphical view of an A-Scan computer display showing the magnetic flux leakage data depicted in FIG. 4 whereby having only every third channel being displayed to clarify the image of FIG. 3 according to an embodiment of the present invention.
Figure 6:
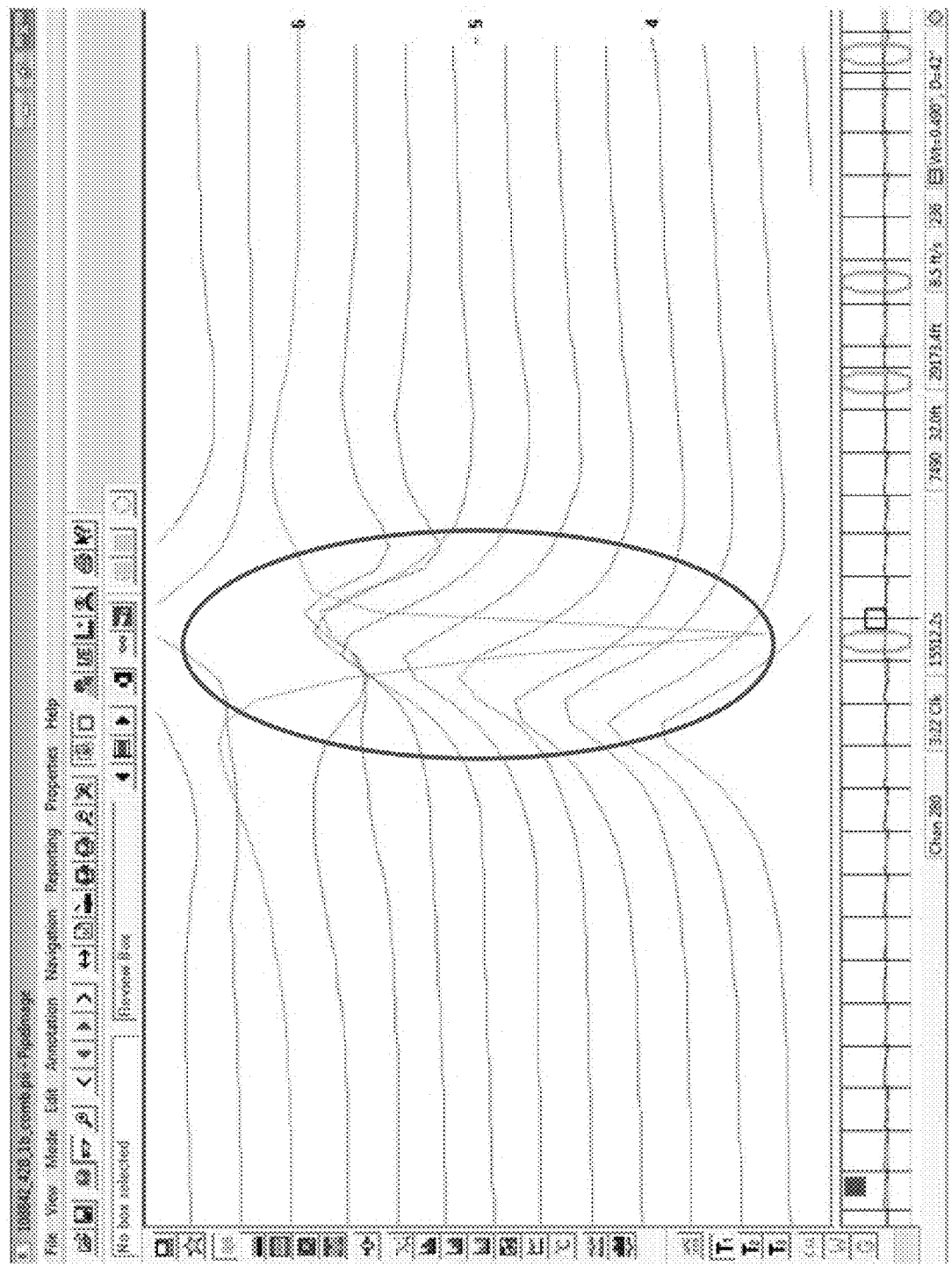
FIG. 6 is a colored graphical view of an A-Scan computer display showing the magnetic flux leakage data depicted in FIG. 4 having only every tenth channel being displayed to clarify the image of FIG. 4 according to an embodiment of the present invention.

In FIG. 5, the display of FIG. 4 is clarified further by displaying only every third channel while prominently displaying the high-frequency signal in a distinguishing color. In FIG. 6, the display is further clarified by removing additional background clutter and only displaying every tenth channel and further zooming in on the high-frequency signal such that only about a quarter of the circumference (90 degrees) of the pipeline wall is depicted. The view in FIG. 6 is considered an optimum or desired clarification providing clear delineation of crack-like signals in the A-MFL data.

Figure 7:
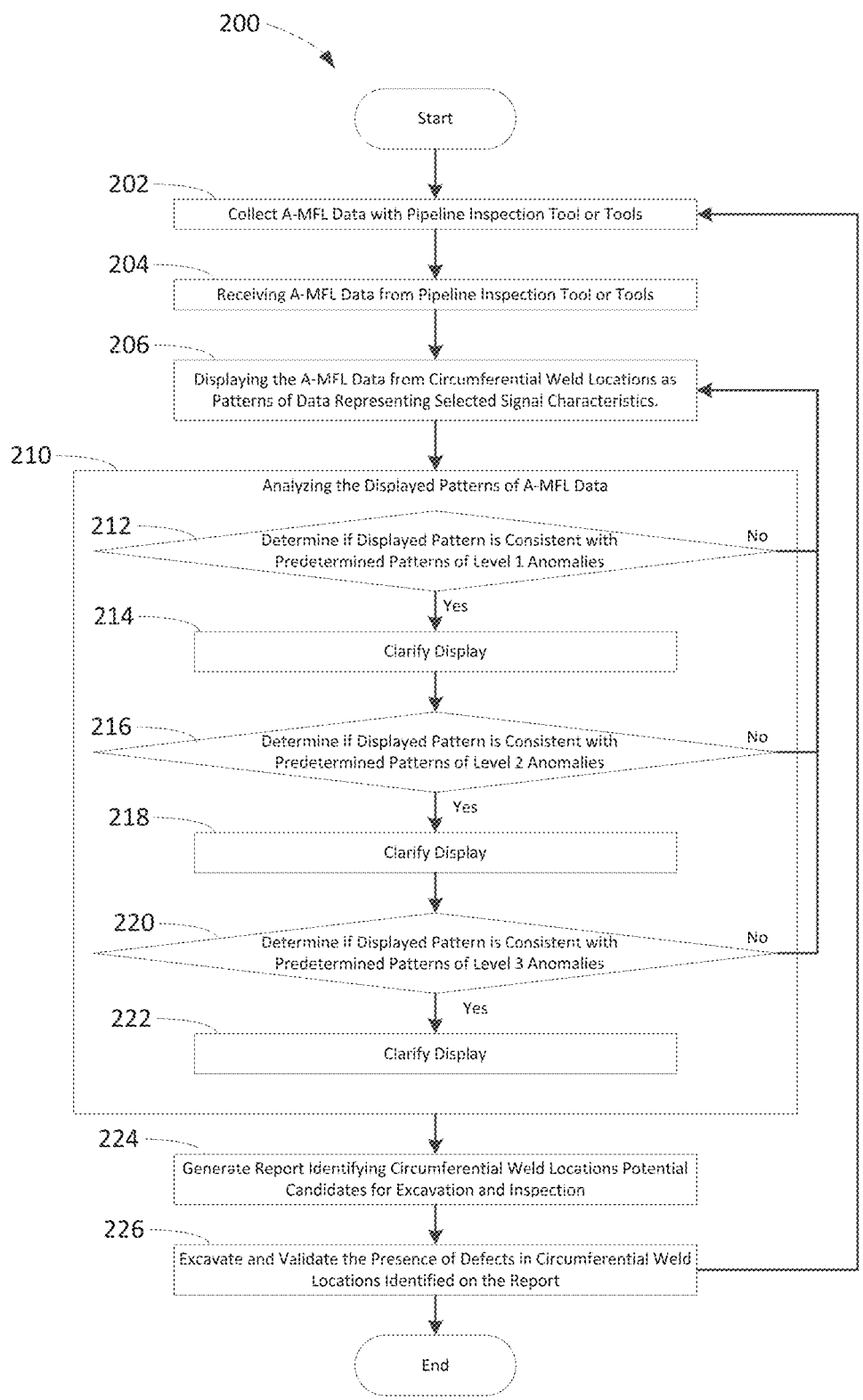
FIG. 7 is a flow chart illustrating another exemplary method of determining locations having an elevated potential of containing threatening anomalies in one or more circumferential pipeline welds according to an embodiment of the present invention.

FIG. 7 illustrates an embodiment of a procedure 200 describes a supplemental screening process applied to ROSEN CDP survey data using the ROSEN ROSOFT for Pipelines or GE-PII "MFL" survey using its PipeImage Display Software, as will be understood by those skilled in the art, to identify pipeline locations with circumferential welds with an elevated potential of containing crack-like defects or other anomalies that can threaten the integrity of the pipeline. Aspects of this procedure 200, for example, can be called a "Wave form analysis or pattern recognition" process and may, in some instances be intended to directly detect crack-like anomalies in circumferential welds, and in other instances may be intended to detect the environmental and operating conditions that could lead to the development of crack-like anomalies. The result of the wave form analysis or pattern recognition process, for example, can be a ranking, e.g., subjective, the anomalies based on relative signal characteristics.

An embodiment of this wave form analysis or pattern recognition process or protocol, for example, identifies circumferential welds with an elevated risk of containing or developing crack-like anomalies. The application or use of this process, in some embodiments, can be sensitive to the pipeline steel properties, the coating condition of the pipeline, the operating environment of the pipeline, the capabilities of the specific pipeline inspection tool, survey tool or ILI tool employed, and the pipeline operating conditions under which the survey was conducted. Thus, when applying the pattern recognition protocol to other conditions, each variable may be considered and adjusted based on the specific application.

The process 200 begins with the collection of A-MFL data (step 202) from a pipeline including circumferential welds. The data is collected from one or more pipeline inspection tools, and in some embodiments, this step may be performed by an ILI vendor providing a more general assessment of pipeline conditions. For example, in some embodiments, the A-MFL data includes data received from the ROSEN CDP pipeline inspection tools.

Next, A-MFL data is received by one or more processors (step 204) from the one or more pipeline inspection tools. The processor identifies segments of the A-MFL data that contain representations of circumferential welds and displays images representing these segments of data (step 206) on one or more displays, such as, for example an LCD computer screen. The A-MFL data is displayed as one or more selected patterns of data representing selected characteristics of a signal detected by the pipeline inspection tool from a wall of the pipeline. In some embodiments, the selected patterns of data include A-Scan images whereby adjacent lines representing signal characteristics representative of a degree of metal present at a location in the pipeline wall, as in the A-scan images of FIGS. 2-6 discussed above. In some embodiments, the selected patterns can include representations of pipeline conditions over a full 360 degree circumference of the pipeline as in the A-scan image of FIG. 2. In other embodiments, the selected patterns of data include contrasting colors, smooth waveforms, erratic/non-erratic patterns, or symmetrical patterns for representing the selected signal characteristics.

Once displayed, the A-MFL data is analyzed (step 210). The analysis, for example, can include a determination of whether the displayed pattern is consistent with predetermined patterns of level-one anomalies (step 212). To make this determination, an analyst may visually inspect the displayed image and assess the similarities and differences between the displayed image and the target pattern, or the pattern can be electronically compared with side-by-side or overlays of known patterns on one or more displays as understood by those skilled in the art. For some embodiments of the present invention, analysts, operators or implementers performing an embodiment of a pattern recognition scan, as understood by those skilled in the art, desirably have some familiarity with pipelines, pipeline construction techniques, ILI tools and tool data and preferably have a working knowledge of pipeline inspection tools. In other embodiments, one or more processors makes the determination, and an analyst further can confirm the determination, if desired, by viewing displayed patterns of data. Generally, the predetermined patterns of level-one anomalies may include features distinguishable from adjacent features such as the features encircled in the A-scan image of FIG. 2. If no level-one anomalies can be identified in a displayed image, the process 200 returns to step 206, and another segment of data representing a different circumferential weld or another portion of the same circumferential weld is displayed. If a level-one anomaly is identified, the process 200 proceeds to clarify the displayed image (step 214). In some embodiments, the clarification of step 214 includes enlarging or zooming in on the image of the level-one anomaly identified with software tools associated with the display.

Once the image is clarified, the analysis includes a determination of whether the displayed pattern is consistent with predetermined patterns of level-two anomalies (step 216). Again, if no level-two anomalies can be identified in the displayed image as clarified in step 214, the process 200 returns to step 206. If a level-two anomaly is identified, the process 200 proceeds to further clarify the displayed image (step 218). The clarification of step 218 includes further enlarging and distinguishing relevant portions of the displayed image, such as the channels identified by a distinct and distinguishing color FIG. 4. In some embodiments, level-two anomalies include those warranting field investigations for inspection or repair. The analysis continues to a determination of whether the displayed pattern is consistent with predetermined patterns of level-three anomalies (step 220). Again, if no level-three anomalies can be identified in the displayed image as clarified in step 218, the process 200 returns to step 206. If a level-three anomaly is identified, the process 200 proceeds to further clarify the displayed image (step 222). The clarification of step 218 includes further enlarging the relevant portions of the image and removing representations of data deemed to be irrelevant. The resulting images from step 222 may include the A-scan images of FIGS. 5 and 6.

Because different pipelines, for example, may require unique software or program product display values due to differences in magnetic characteristics, diameter, wall thickness, grade, and tool speed during the actual inspection, for example. Thus, step 210, in some embodiments, includes applying one or more pipeline variable characteristics to the magnetic flux leakage data being displayed on the one or more displays. The display software utilized as part of embodiments of the present invention, for example, can have an icon, button or other user interface on the display that, when clicked or operated, automatically sets the display values for displaying a particular portion of the circumference of the pipeline.

Once each of the images selected for analysis is assessed and the appropriate images have been characterized as level-one, 2 or 3, an excavation validation report is generated (step 224) identifying locations of circumferential welds containing anomalies potentially threatening the structural integrity of the pipeline. The excavation and validation report may include indications of the levels assigned to the images, and may include the images themselves.

An embodiment of the wave form analysis or pattern recognition process or protocol, as applied to this complex anomaly discrimination, should include and may require confirmation and validation of process applicability in each case. The confirmation can minimally include several validation excavations utilizing "highest level" NDE methods and, in some cases, may require removal of appropriate samples for destructive metallurgical evaluation in a laboratory. A site excavation is requested or performed (step 226) for at least one of the locations identified in the excavation and validation report.

Based on the results of any or several validation excavations performed, the predetermined patterns of data indicative of level-one, 2 or 3 anomalies may be refined and the process 200 returns to step 202 where additional circumferential welds may be evaluated. In all cases the results of field investigations can be reported to appropriate pipeline management personnel and can be compared to the assessment.

Figure 8:
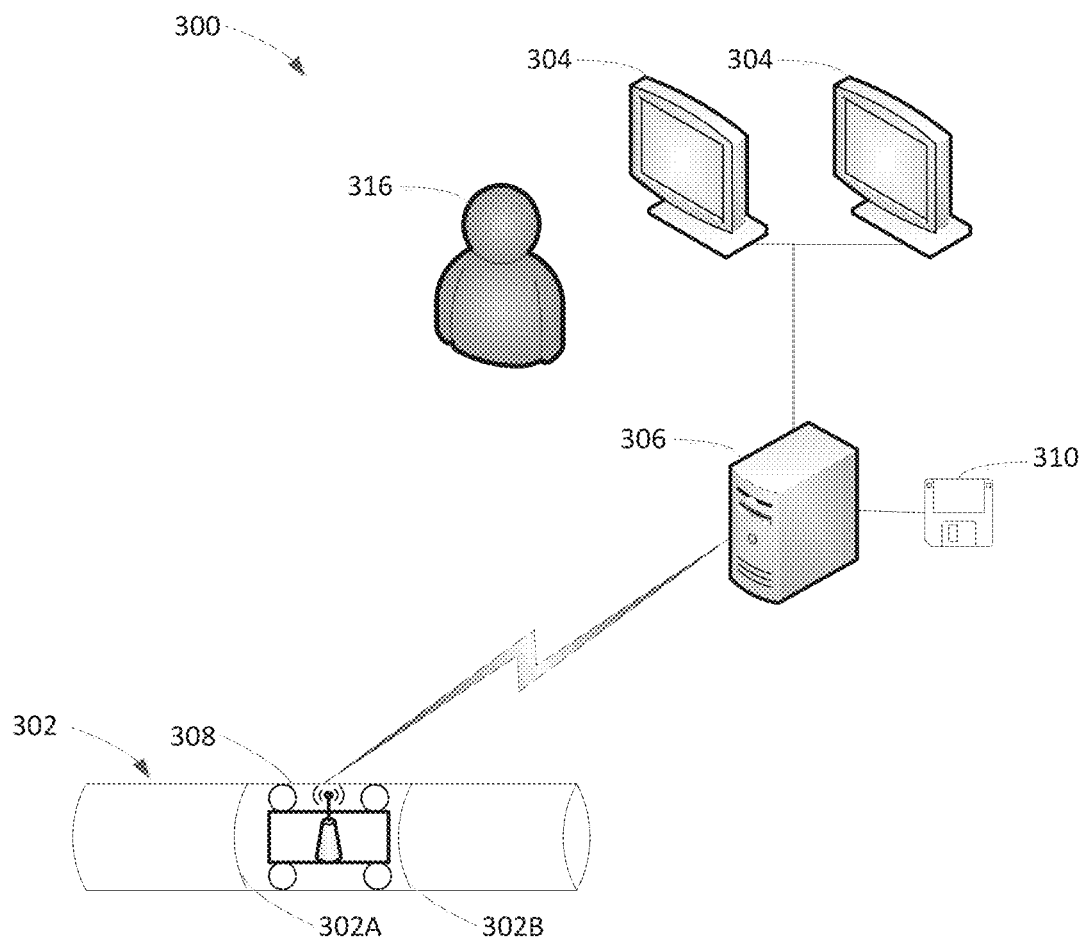
FIG. 8 is a schematic view of a machine to detect and locate anomalies in circumferential pipeline welds having an elevated potential of threatening the structural integrity of the pipeline according to an embodiment of the present invention.

FIG. 8 illustrates an embodiment of a machine 300 to detect and characterize anomalies in circumferential welds 302A and 302B of a longitudinally extending pipeline 302 positioned to transport fluids associated with energy or other resources therethrough. For example, an embodiment of a machine can include one or more displays 304, one or more processors 306 in communication with one or more pipeline inspection survey tools 308, and non-transitory storage media 310 having one or more computer programs stored thereon and readable by the one or more processors 306. The one or more computer programs can include a set of instructions that, when executed by the one or more processors 306, causes the one or more processors 306 to perform the operations of: (i) receiving, in a first process, MFL data from the one or more pipeline inspection survey tools 308 related to the one or more circumferential welds, weld 302A for example, of one or more longitudinal pipelines 302, (ii) displaying, in a second process, the MFL data on the one or more displays 304 as one or more selected patterns of data representing selected signal characteristics of the circumferential weld 302A, (iii) analyzing, in a third process, the MFL data responsive to the selected signal characteristics and one or more predetermined patterns of the MFL data of the circumferential weld 302A being displayed on the one or more displays 304, the one or more predetermined patterns of the MFL data being indicators of anomalies in the circumferential weld 302A potentially threatening the structural integrity of the pipeline 302, and (iv) generating, in a fourth process, an output identifying a location and characterization of the anomalies identified.

The non-transitory storage media 310, for example, also can serve to store report data to generate excavation validation report data. Also, the non-transitory storage media 310 can be updated with confirmation data including whether confirmation of the presence of anomalies at an excavated site occurred thereby to further assess additional A-MFL data associated with the machine 300.

In some embodiments, a user 316 such as an analyst can view the one or more displays 304 to assess and evaluate the one or more selected patterns of data displayed thereon to confirm a determination made by the processor 306. In other embodiments, the user 316 can facilitate the determination by providing an input to the one or more processors 306 based on an assessment made by viewing the one or more displays 304.

It is to be understood by those skilled in the art that the invention is not limited to the exact details of construction, operation, exact materials, or embodiments shown and described, as modifications and equivalents will be apparent to one skilled in the art. For example, although discussed as steps in a computerized process, steps of the present invention may also be accomplished manually. In addition, although aspects of the present invention have been described with respect to a computer, a computer device, a computer machine, or processor executing program product or software that directs the functions of embodiments of the present invention, it should be understood by those skilled in the art that the present invention can be implemented as a program product for use with various types of data processing machines as well. Programs defining the functions of embodiments of the present invention, for example, can be delivered to a data processing machine via a variety of signal-bearing media, which include, without limitation, non-rewritable storage media (e.g., CD-ROM, DVD-ROM, or BluRay), rewritable storage media (e.g., floppy disks, hard drive disks, CD-R, rewritable ROM media, or rewritable BluRay), and communication media, such as digital and analog networks. It should be understood, therefore, that such signal-bearing media, when carrying or embodying computer readable instructions that direct the functions of embodiments of the present invention, represent alternative embodiments of the present invention.

This application claims priority to and the benefit of U.S. Provisional Patent Application Ser. No. 61/864,095, titled "System, Method and Computer Medium Having Computer Program to Detect and Evaluate Structural Anomalies in Circumferentially Welded Pipelines" filed on Aug. 9, 2013, which hereby is incorporated herein by reference in its entirety. This application also is a continuation-in-part of co-pending U.S. patent application Ser. No. 14/039,360 titled "System, Method and Computer Medium Having Computer Program to Determine Presence of Stress Corrosion Cracking in Pipelines With Pattern Recognition" filed on Sep. 27, 2013, which claims priority to and the benefit of U.S. Provisional Patent Application Ser. No. 61/706,575 (now expired) filed on Sep. 27, 2012. This application also is a continuation-in-part of co-pending U.S. patent application Ser. No. 12/953,720 titled "Computer-Implemented Method to Screen for Longitudinal-Seam Anomalies" filed on Nov. 24, 2010, which is a continuation of then pending U.S. patent application Ser. No. 12/270,432, a continuation of then pending U.S. patent application Ser. No. 12/949,896, and a continuation of co-pending U.S. patent application Ser. No. 12/950,118. This application also is a continuation-in-part of co-pending U.S. patent application Ser. No. 12/950,118 titled "System to Screen for Longitudinal-Seam Anomalies" filed on Nov. 19, 2010, which is a continuation of then U.S. patent application Ser. No. 12/270,432. This application also is a continuation-in-part of U.S. patent application Ser. No. 12/949,896 (now U.S. Pat. No. 8,140, 273) titled "Program Product to Screen for Longitudinal-Seam Anomalies" filed on Nov. 19, 2010, which is a divisional of then U.S. patent application Ser. No. 12/270,432. This application also is a continuation-in-part of U.S. patent application Ser. No. 12/270,432 (now U.S. Pat. No. 7,899,628) titled "System, Method and Program Product to Screen for Longitudinal-Seam Anomalies" filed on Nov. 13, 2008, which claims priority to and the benefit of U.S. Provisional Patent Application Ser. No. 61/008,822 (now expired) filed on Dec. 21, 2007. The contents of the above-identified applications hereby are incorporated herein by reference in their entireties.

In the drawings and specification, there have been disclosed illustrative embodiments of the invention and, although specific terms are employed, they are used in a generic and descriptive sense only and not for the purpose of limitation. Accordingly, the invention is therefore to be limited only by the scope of the appended claims.

The invention claimed is:

1. A method of detecting and evaluating anomalies in circumferential welds of a longitudinally extending pipeline for the transport of fluids associated with energy therethrough, the method comprising:
    receiving, in a first process, magnetic flux leakage data from one or more pipeline inspection survey tools, the magnetic flux leakage data including data being associated with one or more circumferential welds of one or more longitudinal pipelines;
    displaying, in a second process, the magnetic flux leakage data on the one or more displays as one or more A-Scan images wherein each of a plurality of channels is represented by a respective one of a plurality of individual lines, and wherein deviations in paths of the individual lines represent an excess or absence of metal in the structure of the one or more longitudinal pipelines;
    identifying, in a third process, one or more weld regions in the one or more A-Scan images including the magnetic flux leakage data representing the one or more circumferential welds;
    analyzing, in a fourth process, the magnetic flux leakage data within the one or more weld regions of the one or more A-Scan images being displayed on the one or more displays by making a determination whether or not anomalous regions can be detected within the one or more weld regions that include an individual line or individual lines that deviate from respective paths in a manner dissimilar to a background array of lines; and
    generating, in a fifth process, an output identifying a location of any of the one or more circumferential welds corresponding to any of the one or more weld regions in which an anomalous region was detected in the fourth process.

2. A method as defined in claim 1, wherein the background array includes lines that deviate in a first direction within the one or more weld regions indicating an excess of metal in the one or more circumferential welds relative to upstream and downstream locations of the one or more circumferential welds, and wherein the anomalous regions include an individual line or individual lines that deviate in a second direction indicating an absence of metal in the one or more circumferential welds.

3. A method as defined in claim 2, wherein the individual line or individual lines that deviate in the second direction represent magnetic flux leakage data signals with a relatively high frequency with respect to a background frequency represented by the background array.

4. A method as defined in claim 1, wherein the second process comprises displaying magnetic flux leakage data representing a full 360 degree circumference of a pipeline wall of the one or more longitudinal pipelines.

5. A method as defined in claim 4, further comprising clarifying, in a sixth process, the one or more weld regions in the one or more A-Scan images, wherein clarifying the one or more weld regions comprises at least one of (i) enlarging a suspected anomalous region within the one or more weld regions, (ii) changing a color of the individual line or individual lines that deviate from respective paths in a manner dissimilar to the background array of lines, and (iii) removing a portion of the background array of lines.

6. A method as defined in claim 5, wherein the suspected anomalous region is enlarged such that magnetic flux leakage data representing only about a quarter of the circumference of the pipeline wall is displayed to clarify the one or more weld regions.

7. A method as defined in claim 5, wherein the portion of the background array of lines is removed such that only every tenth channel represented and displayed to clarify the one or more weld regions.

8. A method as defined in claim 5, wherein the fourth process comprises:
    identifying the suspected anomalous region in magnetic flux leakage data representing the full 360 degree circumference the pipeline wall and making a first determination that the suspected anomalous region is consistent with a first set of predetermined patterns of individual lines indicative of a level-one anomaly;
    enlarging the suspected anomalous region to display a clarified image representing only a portion of the circumference the pipeline wall; and
    making a second determination whether or not the clarified image is consistent with a second set of predetermined patterns of individual lines indicative of a level-two anomaly.

9. A method as defined in claim 8, wherein the fourth process comprises:
    making the second determination that the clarified image is consistent with the second set of predetermined patterns of individual lines indicative of a level-two anomaly;
    further clarifying the clarified image to display a further clarified image; and
    making a third determination whether or not the further clarified image is consistent with a third set of predetermined patterns of individual lines indicative of a level-three anomaly.

10. A method as defined in claim 9, wherein:
    level-one anomalies are defined to include those anomalies which merit further investigation by additional data analysis;
    level-two anomalies are defined to include those anomalies which merit further investigation by excavation and inspection; and
    level-three anomalies are defined to include those anomalies consistent with crack like defects that potentially threaten the structural integrity of the one or more longitudinal pipelines.

11. A method as defined in claim 1, wherein each channel of magnetic flux leakage data displaying on the one or more displays is represented as an individual line on the one or more displays that extends in a generally horizontal direction from an upstream location to a downstream location.

12. A method of detecting and evaluating anomalies in circumferential welds of a longitudinally extending pipeline for the transport of fluids associated with energy therethrough, the method comprising:

receiving, in a first process, magnetic flux leakage data from the one or more pipeline inspection survey tools, the magnetic flux leakage data being associated with one or more circumferential welds of one or more longitudinal pipelines;

displaying, in a second process, the magnetic flux leakage data on the one or more displays as one or more selected patterns of data representing selected signal characteristics of the one or more circumferential welds, wherein the second process comprises displaying an A-Scan image wherein each of a plurality of channels is represented by a respective one of a plurality of individual lines, and wherein deviations in the paths of the individual lines represent an excess or absence of metal in the structure of the one or more longitudinal pipelines;

analyzing, in a third process, the magnetic flux leakage data of the one or more circumferential welds being displayed on the one or more displays by making a determination whether or not the displayed patterns of data are consistent with one or more predetermined patterns of magnetic flux leakage data, the one or more predetermined patterns of the magnetic flux leakage data being indicators of anomalies within the one or more circumferential welds that are potentially threatening the structural integrity of the pipeline;

generating, in a fourth process, an output identifying a location and characterization of any of the one or more circumferential welds for which the displayed patterns of data was determined to be consistent with the one or more predetermined patterns in the third process; and validating, in a fifth process, the output by excavating one or more of the circumferential welds identified in the output and inspecting the one or more of the circumferential welds excavated to confirm the presence of anomalies within the one or more of the circumferential welds excavated that are potentially threatening the structural integrity of the pipeline.

13. A method as defined in claim 12, further comprising updating, in a sixth process, one or more non-transitory storage media having data associated with the output stored thereon with confirmation data including whether confirmation of the presence of anomalies within the one or more of the circumferential welds excavated that are potentially threatening the structural integrity of the pipeline occurred to thereby further assess additional patterns of magnetic flux leakage data.

14. A method as defined in claim 12, wherein the third process comprises making a first determination that a first set of displayed patterns of data is consistent with a first set of predetermined patterns of magnetic flux leakage data, and characterizing the first set of displayed patterns of data as indicative of a level-one anomaly, and thereafter clarifying the first set of displayed patterns of data to display a second set of displayed patterns of data and making a second determination whether or not the second set of displayed patterns of data is consistent with a second set of predetermined patterns of data.

15. A method as defined in claim 14, wherein the third process comprises making the second determination that the second set of displayed patterns of data is consistent with the second set of predetermined patterns of magnetic flux leakage data, and characterizing the second set of displayed patterns of data as indicative of a level-two anomaly, and thereafter clarifying the second set of displayed patterns of data to display a third set of displayed patterns of data and making a third determination whether or not the third set of displayed patterns of data is consistent with a third set of predetermined patterns of data, and if so, characterizing the third set of displayed patterns of data as indicative of a level-three anomaly.

16. A method as defined in claim 15, wherein one or more circumferential welds represented by displayed patterns of data characterized as indicative of level-two or level-three anomalies in the third process are excavated in the sixth process.

17. A method as defined in claim 15, wherein the output includes images of the displayed patterns of data characterized as indicative of level-two or level-three anomalies in the third process.

18. A method as defined in claim 17, wherein the output includes images of the displayed patterns of data characterized as indicative of level-three anomalies in the third process, and wherein the third set of displayed patterns of data is clarified prior to being included in the output.

19. A method as defined in claim 12, wherein each channel of magnetic flux leakage data displaying on the one or more displays is represented as an individual line on the one or more displays that extends in a generally horizontal direction from an upstream location to a downstream location.

20. A machine to detect and evaluate anomalies in circumferential welds of a longitudinally extending pipeline for the transport of fluids associated with energy therethrough, the machine comprising:

one or more displays;

one or more processors in communication with one or more pipeline inspection survey tools; and one or more non-transitory storage media having one or more computer programs stored thereon and readable by the one or more processors, the one or more computer programs including a set of instructions that, when executed by the one or more processors, causes the one or more processors to perform the operations of:

receiving, in a first process, magnetic flux leakage data from the one or more pipeline inspection survey tools, the magnetic flux leakage data being associated with one or more circumferential welds of one or more longitudinal pipelines;

displaying, in a second process, the magnetic flux leakage data on the one or more displays as one or more selected patterns of data representing selected signal characteristics of the one or more circumferential welds, wherein the second process comprises displaying an A-Scan image wherein each of a plurality of channels is represented by a respective one of a plurality of individual lines, and wherein deviations in the paths of the individual lines represent an excess or absence of metal in the structure of the one or more longitudinal pipelines;

analyzing, in a third process, the magnetic flux leakage data of the one or more circumferential welds being displayed on the one or more displays by making a determination whether or not the displayed patterns of data are consistent with one or more predetermined patterns of magnetic flux leakage data, the one or more predetermined patterns of the magnetic flux leakage data being indicators of anomalies within the one or more circumferential welds that are potentially threatening the structural integrity of the pipeline; and generating, in a fourth process, an output identifying a location and characterization of any of the one or more circumferential welds for which the displayed patterns of data was determined to be consistent with the one or more predetermined patterns in the third process.

21. A machine as defined in claim 20, wherein the predetermined patterns of magnetic flux leakage data include deviations in the paths of anomalous individual lines that represent magnetic flux leakage data signals with a relatively high frequency with respect to a background frequency represented by a background array of individual lines, the anomalous individual lines indicative of the absence of metal in the one or more circumferential welds.

22. A machine as defined in claim 21, wherein the third process further comprises clarifying the A-Scan image by distinguishing the anomalous individual lines representing magnetic flux leakage data signals with a relatively high frequency with a distinctive color to more prominently display the selected lines within the background array of individual lines.

23. A machine as defined in claim 22, wherein the third process further comprises clarifying the A-Scan image by removing selected ones of the background array of individual lines indicative of the presence of an excess metal associated with the one or more circumferential welds.

24. A machine as defined in claim 20, wherein the third process comprises making a first determination that a first set of displayed patterns of data is consistent with a first set of predetermined patterns of magnetic flux leakage data, and characterizing the first set of displayed patterns of data as indicative of a level-one anomaly, and thereafter clarifying the first set of displayed patterns of data to display a second set of displayed patterns of data and making a second determination whether or not the second set of displayed patterns of data is consistent with a second set of predetermined patterns of data.

25. A machine as defined in claim 24, wherein clarifying the first set of displayed patterns of data comprises at least one of (i) enlarging a portion of the first set of displayed patterns of data, (ii) changing a color of a portion of the first set of displayed patterns of data, and (iii) removing a portion of the first set of displayed patterns of data.

26. A machine as defined in claim 25, wherein each channel of magnetic flux leakage data displaying on the one or more displays is represented as an individual line on the one or more displays that extends in a generally horizontal direction from an upstream location to a downstream location.

27. Non-transitory storage medium having one or more computer programs stored thereon and readable by one or more processors, the one or more computer programs including a set of instructions that, when executed by the one or more processors, causes the one or more processors to perform the operations of:

receiving, in a first process, magnetic flux leakage data from one or more pipeline inspection survey tools, the magnetic flux leakage data being associated with one or more circumferential welds of one or more longitudinal pipelines;

displaying, in a second process, the magnetic flux leakage data on one or more displays as one or more selected patterns of data representing selected signal characteristics of the one or more circumferential welds, wherein the second process comprises displaying an A-Scan image wherein each of a plurality of channels is represented by a respective one of a plurality of individual lines, and wherein deviations in the paths of the individual lines represent an excess or absence of metal in the structure of the one or more longitudinal pipelines;

analyzing, in a third process, the magnetic flux leakage data of the one or more circumferential welds being displayed on the one or more displays by making a determination whether or not the displayed patterns of data are consistent with one or more predetermined patterns of magnetic flux leakage data, the one or more predetermined patterns of the magnetic flux leakage data being indicators of anomalies within the one or more circumferential welds that are potentially threatening the structural integrity of the pipeline; and generating, in a fourth process, an output identifying a location and characterization of any of the one or more circumferential welds for which the displayed patterns of data was determined to be consistent with the one or more predetermined patterns in the third process.

28. Non-transitory storage medium as defined in claim 27, wherein the deviations in the paths of the individual lines representing an excess of metal are upwardly oriented deviations, and wherein the deviations in the paths of the individual lines representing an absence of metal are downwardly oriented deviations.

29. Non-transitory storage medium as defined in claim 27, wherein the third process comprises making first, second and third determinations whether or not the displayed patterns of data are consistent with one or more predetermined patterns of magnetic flux leakage data, and wherein the displayed patterns of data are clarified between the first, second and third determinations.

30. Non-transitory storage medium as defined in claim 29, wherein the displayed patterns of data are clarified by at least one of (i) enlarging a portion of the displayed patterns of data, (ii) changing a color of a portion of the displayed patterns of data, and (iii) removing a portion of the displayed patterns of data.

31. Non-transitory storage medium as defined in claim 29, wherein the fourth process comprises generating an output including images of the displayed patterns of data that were clarified in the third process.

32. Non-transitory storage medium as defined in claim 31, wherein each channel of magnetic flux leakage data displaying on the one or more displays is represented as an individual line on the one or more displays that extends in a generally horizontal direction from an upstream location to a downstream location.

* * * * *

UNITED STATES PATENT AND TRADEMARK OFFICE
CERTIFICATE OF CORRECTION

PATENT NO. : 10,546,372 B2  
APPLICATION NO. : 14/299650  
DATED : January 28, 2020  
INVENTOR(S) : Noel Duckworth and Tony Wright Page 1 of 1

It is certified that error appears in the above-identified patent and that said Letters Patent is hereby corrected as shown below:

In the Claims

In Claim 1, Column 13, Line 28 should read:
-- data on one or more displays as one or more A-Scan --

In Claim 12, Column 15, Line 7 should read:
-- data on one or more displays as one or more --

Signed and Sealed this
Tenth Day of March, 2020

Andrei Iancu
*Director of the United States Patent and Trademark Office*